US007846097B2

(12) United States Patent
Jones et al.

(10) Patent No.: US 7,846,097 B2
(45) Date of Patent: *Dec. 7, 2010

(54) MEASURING TRANSDUCER MOVEMENT METHODS AND SYSTEMS FOR MULTI-DIMENSIONAL ULTRASOUND IMAGING

(75) Inventors: Paul H. Jones, Mercer Island, WA (US); Paul D. Freiburger, Seattle, WA (US); Craig B. Robinson, Redmond, WA (US); Stephen P. Czenszak, Willoughby, OH (US); Christian Deforge, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 133 days.

This patent is subject to a terminal disclaimer.

(21) Appl. No.: 12/209,964

(22) Filed: Sep. 12, 2008

(65) Prior Publication Data

US 2009/0005680 A1 Jan. 1, 2009

Related U.S. Application Data

(60) Division of application No. 11/590,569, filed on Oct. 30, 2006, now Pat. No. 7,597,664, which is a continuation of application No. 10/372,423, filed on Feb. 20, 2003, now Pat. No. 7,150,716.

(51) Int. Cl.
*A61B 8/00* (2006.01)
(52) U.S. Cl. .................................................... 600/437
(58) Field of Classification Search ................. 600/437; 343/356; 73/342; 356/614
See application file for complete search history.

(56) References Cited

U.S. PATENT DOCUMENTS

| 4,794,384 | A | | 12/1988 | Jackson |
| 5,127,409 | A | | 7/1992 | Daigle |
| 5,353,790 | A | * | 10/1994 | Jacques et al. ............... 600/315 |
| 5,582,173 | A | | 12/1996 | Li |
| 5,655,535 | A | | 8/1997 | Friemel et al. |
| 5,876,342 | A | | 3/1999 | Chen et al. |
| 5,899,861 | A | | 5/1999 | Friemel et al. |
| 5,924,991 | A | | 7/1999 | Hossack et al. |
| 5,928,151 | A | | 7/1999 | Hossack et al. |
| 5,935,071 | A | | 8/1999 | Shcneider et al. |
| 6,246,482 | B1 | | 6/2001 | Kinrot et al. |

(Continued)

OTHER PUBLICATIONS

"Three Channel Optical Incremental Encoder Modules," located on Hewlett Packard website; http://www.secomtel.com/UpFilesPDF/PDF/Agilent/PDF_DOCS/ISONCONT/02_MOTN/2_52_62.PDF, printed on Aug. 17, 2005; 11 pages.

*Primary Examiner*—Brian Casler
*Assistant Examiner*—Jonathan G Cwern

(57) ABSTRACT

Methods and systems for measuring transducer movement are provided. For example, free-hand scanning for three-dimensional imaging is provided. An optical sensor within the transducer measures motion along the skin surface similar to measuring movement of a personal computer mouse with an optical sensor. Alternatively or additionally, the transducer is tilted at an angle other than perpendicular to the skin surface generally towards or away from the direction in which the transducer is translated. The transducer is then translated while maintaining the angle. Motion to or from the transducer is measured, and a component of the motion measured while the transducer is maintained at an angle is parallel to the direction of translation. The component of motion is angle corrected and used to determine a distance of travel.

16 Claims, 2 Drawing Sheets

U.S. PATENT DOCUMENTS

| | | |
|---|---|---|
| 6,330,057 B1 | 12/2001 | Lederer et al. |
| 6,554,771 B1 | 4/2003 | Buil et al. |
| 6,699,191 B2 | 3/2004 | Brock-Fisher |
| 7,150,716 B2 | 12/2006 | Jones et al. |
| 2007/0043293 A1 | 2/2007 | Jones et al. |
| 2009/0012396 A1 | 1/2009 | Jones et al. |

* cited by examiner

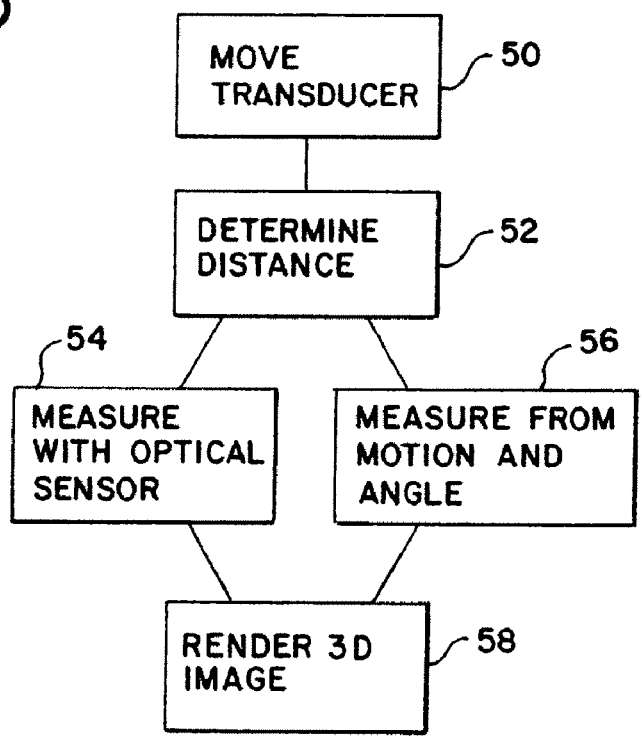
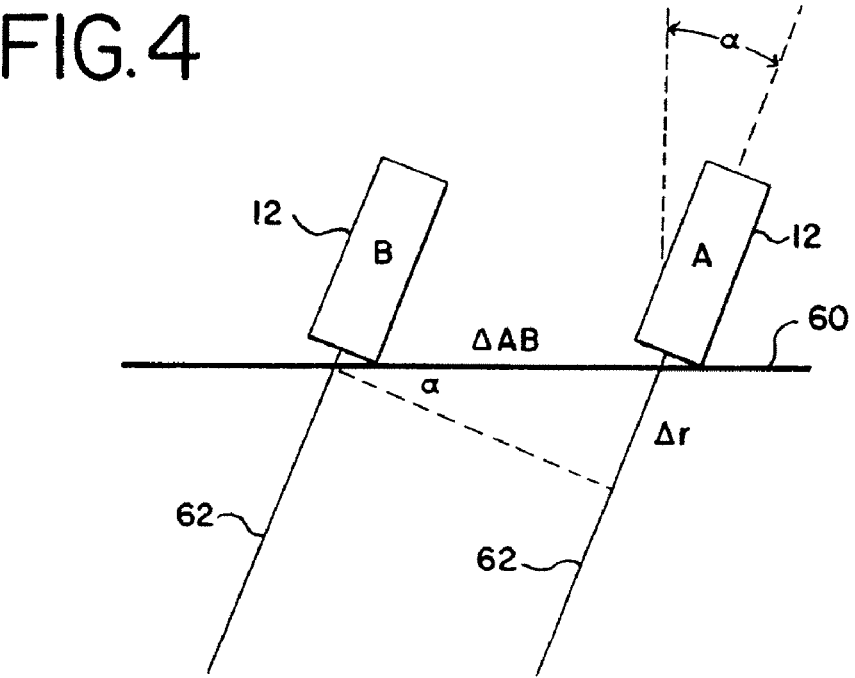

MEASURING TRANSDUCER MOVEMENT METHODS AND SYSTEMS FOR MULTI-DIMENSIONAL ULTRASOUND IMAGING

RELATED APPLICATIONS

The present patent document is a divisional of U.S. application Ser. No. 11/590,569, now U.S. Pat. No. 7,597,664, filed Oct. 30, 2006, which is a continuation of U.S. application Ser. No. 10/372,423, now U.S. Pat. No. 7,150,716, filed Feb. 20, 2003, which are both hereby incorporated by reference.

BACKGROUND

This invention relates to multi-dimensional ultrasound imaging. In particular, methods and systems for free-hand or user operated scanning for three-dimensional (3D) ultrasound imaging are provided.

For 3D ultrasound imaging, a one-dimensional linear array transducer may be used to acquire a plurality of two-dimensional frames of data or images. A three-dimensional volume is scanned by obtaining a plurality of two-dimensional images in different planes. For example, the transducer is held in one location and rotated about an azimuthal axis to scan part of a cylindrical volume. Another example is translating the transducer along an elevation dimension or perpendicular to the array of elements over the surface of the skin. Knowing the relative positions of each scan plane to other scan planes results in more accurate three-dimensional imaging. However, one-dimensional linear arrays provide limited information of scan plane position relative to other scan planes, leading to uncertainty and poor quality three-dimensional representations.

Various methods and devices have been developed for determining the relative position of scan planes. The decorrelation of ultrasound data from one scan plane relative to ultrasound data of an adjacent scan plane may indicate a distance between scan planes, such as disclosed in U.S. Pat. No. 5,876,342, the disclosure of which is incorporated herein by reference. A mechanical structure to mount the transducer may be used to accurately measure or position the transducer for scanning each of spaced scan planes, but such brackets or mountings are difficult, time consuming and cumbersome. Magnetic position sensors or gyroscopes within the transducer provide signals indicating the movement and orientation of the transducer for determining the position of scan planes. These types of sensors may add undesirable weight and complexity to the transducer and metallic objects in the examination area may adversely affect the performance of magnetic position sensors. Cameras, infrared sensors or other sensor positioned within a room for ultrasound scanning remotely identify the position of the transducer on the patient or LEDs on the transducer on the patient, but obstructions may interfere with these devices.

BRIEF SUMMARY

The present invention is defined by the following claims, and nothing in this section should be taken as a limitation on these claims. By way of introduction, the preferred embodiments described below include methods and systems for measuring transducer movement in multi-dimensional ultrasound imaging. For example, free-hand scanning for three-dimensional imaging is provided. An optical sensor within the transducer measures motion along the skin surface similar to measuring movement of a personal computer mouse with an optical sensor. Alternatively or additionally, the transducer is tilted at an angle other than perpendicular to the skin surface generally towards or away from the direction in which the transducer is translated. The transducer is then translated while maintaining the angle. Motion to or from the transducer is measured, and a component of the motion measured while the transducer is maintained at an angle is parallel to the direction of translation. The component of motion is angle corrected and used to determine a distance of travel.

In a first aspect, a system for measuring transducer movement for multi-dimensional ultrasound imaging is provided. An optical sensor connects with the transducer. A processor is operable to determine movement of the transducer in response to a signal from the optical sensor.

In a second aspect, a method for measuring transducer movement for multi-dimensional ultrasound imaging is provided. The transducer is moved. A distance of movement of the transducer is determined with an optical sensor responsive to patient tissue.

In a third aspect, a method for measuring transducer movement for multi-dimensional ultrasound imaging is provided. A transducer is positioned at an angle other than perpendicular to skin surface. At least a portion of the transducer is translated on the skin surface. A distance of motion of the transducer during the translation is measured from ultrasound data. The distance is a function of the angle.

In a fourth aspect, a system for measuring transducer movement for multi-dimensional ultrasound imaging is provided. The system includes a transducer. A processor is operable to determine a distance between scan plane positions as a function of a substantially maintained transducer angle other than perpendicular to a skin surface at each scan plane position and as a function of measured motion from ultrasound data.

Further aspects and advantages of the invention are discussed below in conjunction with the preferred embodiments.

BRIEF DESCRIPTION OF THE DRAWINGS

The components and figures are not necessarily to scale, emphasis instead being placed upon illustrating the principles of the invention. Moreover, in the figures, like reference numerals designate corresponding parts throughout the different views.

FIG. 3 is flowchart diagram of one embodiment of a method for measuring transducer movement for three-dimensional ultrasound imaging; and FIG. 4 is a graphical representation according to one embodiment of a transducer translated along the skin surface at an angle.

DETAILED DESCRIPTION OF THE DRAWINGS AND PRESENTLY PREFERRED EMBODIMENTS

Free-hand scanning for multi-dimensional imaging allows the operator to translate or rotate the transducer. The movement of the transducer allows scanning of multiple two-dimensional planes within a volume. To provide geometric accuracy for the relative positioning of the various two-dimensional planes, an optical sensor is positioned on the transducer or motion data is measured while scanning with the transducer at a non-perpendicular angle to the skin surface. Either technique for determining the position of scan planes is used independently or in combination. When used in combination, the scan plane positions are averaged, combined or used as verification. Each of these two approaches will be discussed below with some description, such as three-dimensional rendering and the ultrasound system, being either the same for both.

Figure 1:
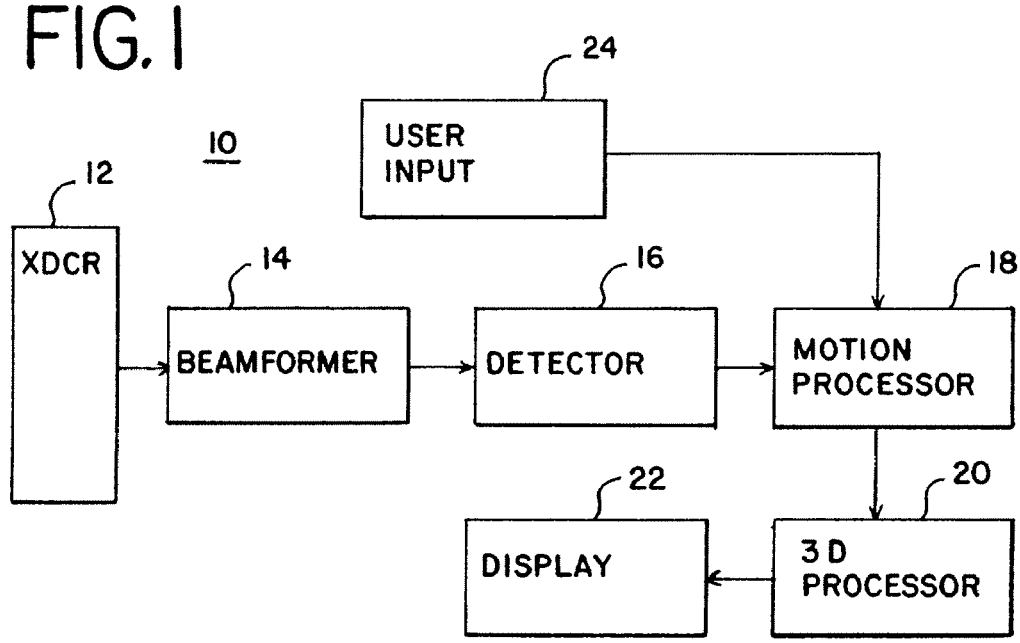
FIG. 1 is a block diagram of one embodiment of an ultrasound system for multi-dimensional imaging.

FIG. 1 shows one embodiment of an ultrasound system 10 for measuring transducer movement for multi-dimensional ultrasound imaging. The system 10 includes a transducer 12, a beamformer 14, a detector 16, a motion processor 18, a 3D processor 20, a display 22 and a user input 24. Additional, different or fewer components may be provided, such as using a control processor to implement both the motion processor 18 and the 3D processor 20.

The transducer 12 comprises a linear or multi-dimensional array of elements, such as PZT elements or CMUT elements. The array of elements is configured as a linear, curved linear or other array for linear, sector, or Vector® imaging. In one embodiment, the transducer 12 is adapted for use on the exterior of a patient or used in a patient's skin surface. For example, the transducer 12 is enclosed within a housing adapted to be held by a user's hand. The transducer 12 is positioned adjacent to the housing surface of the probe such that the transducer is operable to transmit acoustic energy through the housing surface, such as through a lens or acoustic window. The housing surface is generally planar or slightly curved, smooth surface for contacting the pliable skin surface. In other embodiments, the transducer 12 is adapted for insertion within the patient, such as a catheter, transesophageal or endocavity probe. Any of various now known or later developed transducers 12 may be used.

Figure 2A:
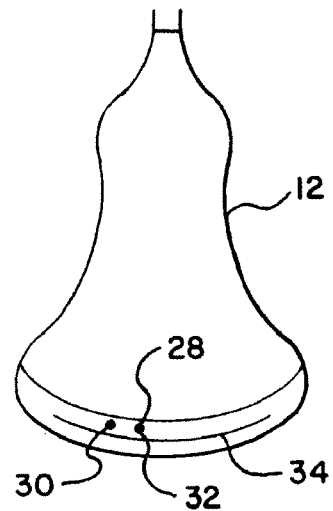
FIGS. 2A and 2B are side and bottom views, respectively, of one embodiment of an ultrasound transducer with an optical sensor.
Figure 2B:
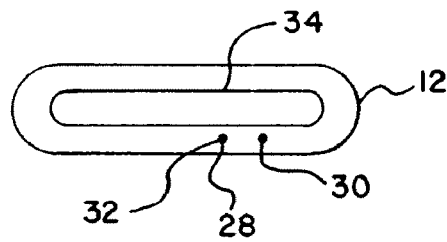

In one embodiment shown in FIGS. 2A and 2B, the transducer 12 includes an optical sensor 28. The optical sensor 28 comprises a light source 30 and a camera 32. In alternative embodiments, the light source 30 is not provided or is separate from the transducer 12. The light source 30 comprises a light emitting diode. The light source 30 emits light at any of various wavelengths in the optical spectrum. In one embodiment, the light source 30 emits light at a wavelength of less than 700 nanometers, such as a blue green LED emitting a wavelength of around 400 nanometers. A red LED emitting a wavelength around 700 nanometers may be used. Shorter wavelengths are more likely to reflect from the skin surface rather than pass through tissue. Alternatively, the patient tissue is coated with ink or another substance for darkening the skin and making it more reflective of a wavelength of light detected by the optical sensor 28.

The camera 32 comprises a complementary metal-oxide semiconductor (CMOS) sensor. In alternative embodiments, a CCD, photodetector cells or other optical wavelength sensor is provided. The light source 30 bounces light off of the skin surface or other tissue onto the camera 32. The camera 32 detects or senses images, such as hundreds or thousands of images every second, at least in part of the wavelength of the light source 30. In one embodiment, the optical sensor 28 comprises the structures and/or methods disclosed in U.S. Pat. Nos. 4,794,384; 6,330,057; and 6,246,482, the disclosures of which are incorporated herein by reference. Any of speckle, phase shifts, phasing, frequency, or other characteristics of received light may be used to detect motion.

The optical sensor 28 is positioned on, within or adjacent to the housing surface of the transducer 12. The optical sensor 28 receives light directed towards the housing surface. By positioning the optical sensor 28 adjacent to an acoustic window 34, the linear array behind the acoustic window 34 or on an outer surface adapted for placement adjacent to or in contact with the tissue surface, the optical sensor 28 is positioned to receive light from the skin surface. In alternative embodiments, the optical sensor 28 is positioned away from the skin surface but directed towards the skin surface for measuring movement of the transducer 12. In yet other alternative embodiments, multiple optical sensors 28 are provided on the transducer 12.

In an alternative embodiment, an adaptor with the optical sensor 28 connects with the transducer and the housing. The adaptor snap fits, latches, screws or otherwise connects with the transducer 12. The adaptor is provided with an acoustic window in one embodiment for connecting between the transducer 12 and the skin surface or tissue surface during use, but in alternative embodiments connects to a side of the transducer 12 for positioning the optical sensor 28 adjacent to the skin surface and adjacent to the surface of the transducer 12 adapted for contact with the skin. In yet other alternative embodiments, the adaptor connects elsewhere on the transducer 12.

The beamformer 14 comprises any of various analog and/or digital circuits for receive and transmit beamforming. The beamformer 14 generates transmit waveforms for the transducer 12, and beamforms ultrasound data from received echo signals in response to various delays and apodization. The detector 16 comprises a B-mode detector, a flow detector, a Doppler detector, a harmonic detector, a contrast agent detector or other now known or later developed detector of information from the beamformed ultrasound data.

The motion processor 18 comprises a general processor, a digital signal processor, an application specific integrated circuit, an analog circuit, a digital circuit, combinations thereof, or any other circuits now known or later developed for determining motion from the ultrasound data or from the optical sensor 28. In the embodiment using the optical sensor 28, the motion processor 18 is housed within the transducer 12, in an adaptor connected with the transducer 12 or with other components of the ultrasound system 10, such as within the data processing path as shown or not within the data processing path. For use with an optical sensor 28, the motion processor 18 comprises a digital signal processor operating at millions of instructions per second (e.g., 18 MIPS) to determine a translation along at least one axis. For example, the motion processor 18 determines the direction on a two-dimensional surface and distance along the direction corresponding to translation of the transducer 12 based on pattern matches. The optical sensor 28 in conjunction with the motion processor 18 may also be operable to determine rotation based on the pattern matching or correlation process.

In the embodiment of detecting motion from ultrasound data acquired with the transducer 12 held at an angle, the motion processor 18 comprises, in part, a flow detector 16 operable to detect motion along a scan line and a same or additional processor operable to determine a component of motion parallel to a skin surface as a function of the motion detected along the scan line. Any combination of single processors or multiple processors provided in one component or spaced throughout the ultrasound system 10 or elsewhere may be used. The motion processor 18 is operable to determine a distance between scan plane positions as a function of a substantially maintained transducer angle other than perpendicular to the skin surface at each scan plane position and as a function of measured motion of translation of the transducer 12 between the scan plane positions. Using a determined velocity, such a Doppler velocity or a cross correlation, the motion processor 18 is operable to measure in plane motion and extract a distance between scan planes from the motion. The motion processor 18 in one embodiment is also operable to render a three-dimensional representation as a function of the distance, but a separate processor may be provided as shown in FIG. 1. In one embodiment, the motion processor 18 operates on detected ultrasound data. In an alternative embodiment, the motion processor 18 receives beamformed ultrasound data prior to detection for determining cross correlation or other indicators of motion.

The user input 24 comprises a keyboard, dedicated keys, software programmable keys, touch screen, knobs, switches, sliders, joystick, trackball, mouse, combinations thereof or any now known or later developed user input devices. In the embodiment for detecting transducer motion based on in scan plane detected motion and the angle of the transducer, the user in input 24 connects with the motion processor 18. The user inputs the angle for holding the transducer. In alternative embodiments, a tilt sensor within the transducer 12 automatically determines the angle, or a fixture is used to position the transducer 12 at a desired angle. In yet other alternative embodiments, the user is instructed to hold the transducer 12 at a particular angle rather than inputting an angle. For either of the optical sensor or angled transducer embodiments, the user input 24 may be used for calibrating the system 10 or motion processor 18.

The three-dimensional processor 20 comprises a processor, a digital signal processor, an application specific integrated circuit, a video card, graphics accelerator, digital circuit, analog circuit, combinations thereof or any other now known or later developed device for rendering a representation of a three-dimensional volume. A two-dimensional image representing a 3D volume is rendered from ultrasound data associated with a plurality of scan planes. The scan planes are spaced within a volume such that the rendering is responsive to the relative positions of the scan planes. The relative positioning of the scan planes is determined as a function of the movement of the transducer 12 or the distance detected by the motion processor 18. In one embodiment, the 3D processor 20 is configurable to perform different types of volume rendering, shading, surface rendering or texture mapping. In other alternative embodiments, the 3D processor 20 comprises a dedicated circuit for performing a particular type of rendering using data interpolated from a Cartesian coordinate, polar, cylindrical or other specific or known grid. The distance or motion information is used to interpolate the data onto the grid.

FIG. 3 shows a flow diagram of one embodiment of a method for measuring transducer movement for three-dimensional ultrasound imaging. The method uses one or both of measuring transducer movement with an optical sensor 28 or measuring transducer movement as a function of a measured motion and angled position of the transducer 12. Other methods with additional, different, or fewer acts may be used.

In act 50, the transducer 12 is positioned for imaging and moved. For example, and as shown in FIG. 4, the transducer 12 is positioned along the surface of the skin 60 in a first position A and moved to a second position B, a change represented by $\Delta AB$. In one embodiment, the transducer 12 is positioned perpendicular to the skin surface 60. In another embodiment, the transducer 12 is positioned at an angle other than perpendicular to the skin surface 60 or other tissue. For example, the transducer 12 is rotated away from a normal to the skin surface by an angle $\alpha$ as shown in FIG. 4, defining a triangle having sides $\Delta AB$, $\Delta r$, and an orthogonal line between the scan planes 62. $\alpha$ can be of any of various angles, such as about 60 degrees. About and substantially are used herein for describing an angle or transducer position to account for user estimation, user changes in transducer position away from intended motion due to the inexactness of user control or free-hand movement along the often bumpy or flexible skin surface, patient breathing, patient movement or other variable. The transducer 12 is at a non-perpendicular angle in the out-of-plane dimension in one embodiment. Where the transducer 12 is positioned at an angle to the normal as shown in FIG. 4, a linear array of the transducer 12 is positioned such that the both ends of the array are about a same distance from a skin surface, such as associated with rotating the transducer 12 away from the normal around the azimuthal axis. As a result, the scan planes 62 are seen edge on in FIG. 4 (e.g. the scan planes extend perpendicular to the plane of the page or paper). Alternatively, one end of an array is rotated further away from the skin surface than the other end.

For the embodiment using the angled transducer 12 as shown in FIG. 4, at least a portion of the transducer 12 is translated on the skin surface 60. For example, the transducer 12 is translated along an elevation dimension from the position A to the position B. The angle $\alpha$ is substantially maintained during translation or at least at each location where a scan plane 62 is acquired. As another example, the transducer 12 is rotated about a center axis extending along the range dimension while maintaining the range dimension axis at an angle away from the normal to the skin surface 60 or other tissue surface. Any one or combinations of rotational, linear and two-dimensional translation may be used.

In act 52, the distance, motion, rotation, direction or other characteristic of transducer movement is determined. One or both of the two different acts 54 and 56 may be used for determining the motion or other characteristic. In act 56 the motion of the transducer 12 is measured from ultrasound data. The motion is determined as a function of the angle of the transducer 12 away from perpendicular. The ultrasound data is used to determine motion along or within the scan plane 62, such as a long one or more scan lines. For example, a Doppler velocity is detected along one or more depths within a scan line or the imaging plane 62. As another example, a cross correlation of beamformed data prior to detection or after detection is performed. The cross correlation indicates the velocity or motion relative to the transducer 12. Other techniques for determining motion to or away from the transducer 12 may be used. For example, the peak of the cross correlation function between two data sets indicates the velocity along the scan line or image plane 62. The sign of the shift indicates the direction of the motion, indicating the direction of transducer motion.

The component of motion parallel to the skin surface 60 is extracted from the measured motion. For example, the measured motion is divided by the sine of the transducer angle $\alpha$. An average of multiple measurements, a single measurement, different measurement for different transducer angles or other combinations of measurements may be used. Since the time of acquisition between the two different scan planes 62 is known, the component of motion along the skin surface 60 is converted to a distance between the two scan planes 62. Given the angle and the distance, the relative position of each scan plane 62 to other scan planes is known.

At each transducer position or a range of positions during continuous movement, a two-dimensional scan is performed. The two-dimensional image data may include tissue motion compensation to counteract the motion of the transducer 12 during the two-dimensional scan. For example, a motion relative to different regions within a scan plane is determined. The estimated position of the scan plane is warped or adjusted as a function of the different positions of various scan lines within the image relative to the ideal scan plane position 62. Flow estimation techniques like Doppler, color flow or spectral Doppler measure the motion, or motion is estimated in the time domain by cross correlation or sum of absolute differences calculations. Other calculations or measurements of motion from ultrasound data may be used.

In act 54, the distance or other motion characteristic is measured with the optical sensor 28. The optical sensor 28 is responsive to patient tissue, such as detecting light reflected from or through skin tissue using correlation, phase shift or other techniques for determining a direction and amount of translation of the transducer 12. Using the optical sensor 28, the transducer 12 is positioned perpendicular or non-perpendicular to the tissue surface 60. By directing the optical sensor 28 towards the skin surface, the distance of transducer movement is determined based on the changes in position of the transducer 12 over the skin surface. By positioning the optical sensor 28 adjacent to the transducer 12 or as part of the transducer 12, the distance is determined by a camera facing in the same direction as the transducer 12 or passing over similar skin surfaces. The optical sensor 28 may also detect rotational movement along a single axis or movement along multiple axes in a plane.

Since the transducer 12 may block light from the skin surface adjacent to the camera or optical sensor 28, the optical sensor includes an LED or other light source 30. In one embodiment, light is directed towards the patient tissue and reflected back to the camera 30 of the optical sensor 28. In alternative embodiments, the optical sensor 28 is positioned to receive light reflected from tissue not covered by the transducer 12.

The optical sensor 28 is calibrated by the user or by the manufacturer. In alternative embodiments, empirical testing or other measurements allow programming the optical sensor 28 in the motion processor 18 without further calibration. For calibration, the image characteristics used by the optical sensor 28 are adjusted for known distances across a piece of paper or sample tissue. Calibration may minimize errors in the distance calculation from the optical sensor 28.

In act 58, a three-dimensional representation image is rendered. The three-dimensional representation is rendered as a function of the distance or other motion characteristic. The ultrasound data, such as detected velocity, intensity, energy, power or other data is organized as image data frames for each scan plane position. The ultrasound data comprises scan converted data in a Cartesian coordinate system or polar coordinate data. The image data frames are associated with relative positional information, such as the distance, angle, relative rotation, orientation and/or other positional information. The two-dimensional image frames are either coplanar or non-coplanar, such as two or more rotationally offset planes or two or more planes offset in an elevation position. The positional information provides the relative position among the image data frames so that these frames may be subsequently assembled in a three-dimensional volume, such as along a Cartesian coordinate or a polar coordinate three-dimensional grid. In one embodiment, the positional information comprises three components of position (X, Y, Z) and three components of rotation (about X, about Y and about Z). Other definitions of position and orientation may be used, such as two known points and one origin point on each plane.

The information from the two-dimensional image data frames is converted to the 3D grid, such as regularly (equal) spaced volume grid. Equal spacing allows for efficient calculations and use with low cost visualization software, but unequal spacing may be used. The conversion is performed by interpolation, nearest neighbor selection or other two- or three-dimensional conversion techniques. Alternatively, the representation is rendered from data not converted to a specific 3D grid.

Appropriate data is selected from the 3D grid samples or from data not on the regular 3D grid to provide a desired representation. Any of various three-dimensional imaging techniques may be used, such as harmonic or fundamental data three-dimensional imaging disclosed in U.S. Pat. No. 5,928,151, the disclosure of which is incorporated herein by reference. The selected information is used for surface rendering, volume rendering or other three-dimensional rendering technique. For surface rendering, threshholding or other processes identify one or more surfaces. Once the surfaces are determined, a polygon mesh is formed to represent the surface. The surface is rendered with lighting cues, such as Gouraud or Phong shading.

Any of alpha blending, maximum intensity projection or minimum intensity projection may be used for volume rendering. In response to a user selected or system determined viewing angle, data along ray lines parallel with the viewing angle intersect the 3D data grid. The data along each line is averaged or selected for a minimum or maximum intensity value. By alpha blending or selecting maximum or minimum values along each of the ray lines, a two-dimensional representation of the three-dimensional volume is generated as seen from a particular viewing angle. Other representations associated with a different viewing angles may be generated for rotating the representation for a more three-dimensional appearance.

Either or both of the optical sensor 28 or angled transducer 12 with motion measurement may be used for extended field of view or panoramic imaging. A plurality of coplanar images associated with different transducer positions are acquired. The distance between transducer positions is used to align the images for compositing as an extended field of view.

While the invention has been described above by reference to various embodiments, it should be understood that many changes and modifications can be made without departing from the scope of the invention. For example, any of various perpendicular or angled positions of transducers 12 relative to the skin surface 60 or orientation of the transducer array may be used, including combinations of different angles. A multi-dimensional array, such as 1.25, 1.5, 1.75, 2D arrays may be used. Sensors or brackets in additional to an optical sensor may be used. Transducers 12 without an optical sensor may also be used. Any of various now known or later developed optical sensors using pattern matching or other characteristics for determining a distance may be used. The distance may be a relative spacing without an actual spacing determination.

It is therefore intended that the foregoing detailed description be regarded as illustrative rather than limiting, and that it be understood that it is the following claims, including all equivalents, that are intended to define the spirit and scope of this invention.

We claim:

1. A method for measuring transducer movement for multi-dimensional ultrasound imaging, the method comprising:

positioning a transducer at an angle other than perpendicular to a skin surface;

translating at least a portion of the transducer on the skin surface, wherein translating comprises translating the transducer while substantially maintaining the angle;

measuring, from ultrasound data, a first distance of the transducer translation during translating, the first distance being calculated as a function of a value of the angle; and determining a second distance of the transducer translation with an optical sensor responsive to patient tissue of the skin surface; and determining a translation distance as a function of the first and second distances.

2. The method of claim 1 wherein positioning comprises positioning the transducer at about 60 degrees from perpendicular to the skin surface, the transducer comprising a linear array with both ends of the array about a same distance from the skin surface.

3. The method of claim 1 wherein measuring comprises measuring a first motion along a scan line and determining a second motion parallel to the skin surface as a function of the angle and the first motion.

4. The method of claim 3 wherein the first motion comprises a Doppler velocity detected from ultrasound data along the scan line.

5. The method of claim 3 wherein measuring comprises measuring the first motion in response to a cross-correlation of beamformed data prior to detection.

6. The method of claim 1 further comprising:

determining a scan plane separation distance from the first and second distances; and rendering a three-dimensional representation as a function of the scan plane separation distance.

7. The method of claim 1 wherein determining comprises averaging the first and second distances.

8. The method of claim 1 further comprising:

directing light having a wavelength less than 700 nanometers towards the patient tissue;

wherein determining with the optical sensor comprises determining with the optical surface directed at the skin surface.

9. The method of claim 1 further comprising:

determining a direction within a plane of movement of the transducer, a rotational movement, or combinations thereof.

10. The method of claim 1 further comprising receiving a user indication of the angle.

11. The method of claim 1 wherein translating comprises moving, by free-hand motion, the transducer across the skin surface of a patient.

12. The method of claim 1 further comprising:

scanning a plurality of planes below the skin surface with ultrasound from the transducer, the plurality of planes at different locations within a patient due to the translating.

13. The method of claim 1 wherein determining with the optical sensor comprises directing the optical sensor and a blue-green light source at the skin surface during the translating.

14. The method of claim 1 wherein determining with the optical sensor comprises determining responsive to blue-green light from a blue-green light source reflected from the patient skin.

15. The method of claim 1 wherein determining with the optical sensor comprises determining with light with a wavelength around 400 nanometers.

16. The method of claim 1 further comprising connecting the transducer with the optical sensor using an adaptor.

* * * * *